US012165308B2

(12) United States Patent
Patil et al.

(10) Patent No.: US 12,165,308 B2
(45) Date of Patent: Dec. 10, 2024

(54) AUTOMATIC SLICE SELECTION IN MEDICAL IMAGING

(71) Applicant: KONINKLIJKE PHILIPS N.V., Eindhoven (NL)

(72) Inventors: Ravindra Balasaheb Patil, Bangalore (IN); Rithesh Sreenivasan, Bangalore (IN); Krishnamoorthy Palanisamy, Bangalore (IN); Nagaraju Bussa, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 627 days.

(21) Appl. No.: 17/047,102

(22) PCT Filed: Apr. 12, 2019

(86) PCT No.: PCT/EP2019/059491
§ 371 (c)(1),
(2) Date: Oct. 13, 2020

(87) PCT Pub. No.: WO2019/197644
PCT Pub. Date: Oct. 17, 2019

(65) Prior Publication Data
US 2021/0158526 A1  May 27, 2021

(30) Foreign Application Priority Data
Apr. 13, 2018  (EP) ..................... 18167156

(51) Int. Cl.
*G06T 7/00* (2017.01)
*A61B 1/00* (2006.01)
(Continued)

(52) U.S. Cl.
CPC ...... *G06T 7/0012* (2013.01); *A61B 1/000096* (2022.02); *A61B 5/055* (2013.01);
(Continued)

(58) Field of Classification Search
CPC ................. G06T 7/0012; G06T 7/0016; G06T 2207/10068; G06T 2207/10081;
(Continued)

(56) References Cited

U.S. PATENT DOCUMENTS 9,633,306 B2   4/2017  Liu et al.
10,140,421 B1 * 11/2018  Bernard .................. G01T 1/247
(Continued)

FOREIGN PATENT DOCUMENTS

CN  105640577 A   6/2016
WO  2007018755 A1  2/2007
(Continued)

OTHER PUBLICATIONS

International Search Report and Written Opinion for International Application No. PCT/EP2019/059491, filed Apr. 12, 2019, 14 pages.

*Primary Examiner* — Qun Shen

(57) ABSTRACT

A medical imaging system (100, 300, 400, 700) includes a processor and memory with instructions executable by the processor to receive (200) three-dimensional medical image data (122) comprising multiple slices, receive (202) an imaging modality (124) of the three-dimensional medical image data, receive (204) an anatomical view classification (126) of the three-dimensional medical image data, select (206) a chosen abnormality detection module (130) from a set of abnormality detection modules (128) using the imaging modality and the anatomical view classification, wherein at least a portion of the abnormality detection modules is a convolution neural network trained for identifying if the at least a portion of the multiple slices as either normal or abnormal, classify (208) the at least a portion of the multiple slices as normal or abnormal using the abnormality detection module, and choose (210) a set of selected slices (136) from the multiple slices according to a predetermined selection (Continued)

criteria (134) if a predetermined number of the multiple slices are classified as abnormal.

26 Claims, 7 Drawing Sheets

(51) Int. Cl.

| | | |
|---|---|---|
| A61B 5/055 | (2006.01) | |
| A61B 6/00 | (2024.01) | |
| A61B 6/03 | (2006.01) | |
| A61B 8/08 | (2006.01) | |
| G06F 18/2431 | (2023.01) | |
| G06N 3/08 | (2023.01) | |
| G16H 30/20 | (2018.01) | |
| G16H 30/40 | (2018.01) | |
| G16H 40/20 | (2018.01) | |
| G16H 40/67 | (2018.01) | |
| G16H 50/20 | (2018.01) | |

(52) U.S. Cl.
CPC ............ *A61B 6/5223* (2013.01); *A61B 8/523* (2013.01); *G06F 18/2431* (2023.01); *G06N 3/08* (2013.01); *G06T 7/0016* (2013.01); *G16H 30/20* (2018.01); *G16H 30/40* (2018.01); *G16H 40/20* (2018.01); *G16H 40/67* (2018.01); *G16H 50/20* (2018.01); *A61B 6/032* (2013.01); *A61B 6/037* (2013.01); *G06T 2207/10068* (2013.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/20081* (2013.01); *G06T 2207/20084* (2013.01); *G06V 2201/03* (2022.01)

(58) Field of Classification Search
CPC . G06T 2207/10088; G06T 2207/10104; G06T 2207/10116; G06T 2207/10132; G06T 2207/20081; G06T 2207/20084; G16H 40/67; G16H 40/20; G16H 30/20; G16H 30/40; G16H 50/20; A61B 1/000096; A61B 5/055; A61B 6/5223; A61B 6/032; A61B 6/037; A61B 8/523; G06F 18/2431; G06N 3/08; G06V 2201/03

See application file for complete search history.

(56) References Cited

U.S. PATENT DOCUMENTS

| | | | |
|---|---|---|---|
| 10,223,785 B2 | 3/2019 | Kitamura et al. | |
| 10,499,857 B1* | 12/2019 | Nguyen | G06N 3/045 |
| 10,678,464 B2* | 6/2020 | Zhao | G06F 3/0619 |
| 11,478,226 B2* | 10/2022 | Kezurer | G16H 50/30 |
| 2003/0117279 A1* | 6/2003 | Ueno | G08B 21/0423 |
| | | | 340/523 |
| 2004/0002808 A1* | 1/2004 | Hashimoto | F02D 11/107 |
| | | | 701/107 |
| 2007/0036402 A1* | 2/2007 | Cahill | G06T 7/0012 |
| | | | 382/128 |
| 2007/0165924 A1* | 7/2007 | Nicponski | G06T 7/0012 |
| | | | 382/128 |
| 2009/0234531 A1* | 9/2009 | Sayama | H02J 9/061 |
| | | | 701/31.7 |
| 2010/0246912 A1* | 9/2010 | Periaswamy | G06T 7/0012 |
| | | | 382/128 |
| 2010/0328235 A1* | 12/2010 | Taute | G06F 3/04886 |
| | | | 345/173 |
| 2013/0121548 A1 | 5/2013 | Kovalan | |
| 2014/0161327 A1 | 6/2014 | Motomura et al. | |
| 2015/0076041 A1* | 3/2015 | Irie | B07C 5/00 |
| | | | 209/555 |
| 2016/0328643 A1* | 11/2016 | Liu | G06N 3/045 |
| 2016/0350919 A1 | 12/2016 | Steigauf | |
| 2016/0364528 A1 | 12/2016 | Reicher | |
| 2016/0379363 A1* | 12/2016 | Kitamura | A61B 1/0005 |
| | | | 600/371 |
| 2017/0004625 A1* | 1/2017 | Kamiyama | G06T 7/0016 |
| 2018/0218516 A1* | 8/2018 | Reda | G06N 3/08 |
| 2018/0292806 A1* | 10/2018 | Kawatake | G05B 19/41875 |
| 2019/0073764 A1* | 3/2019 | Wong | G06N 20/00 |
| 2019/0198156 A1* | 6/2019 | Madani | G06N 3/082 |

FOREIGN PATENT DOCUMENTS

| | | |
|---|---|---|
| WO | 2016124763 A1 | 8/2016 |
| WO | 2017011532 A1 | 1/2017 |

* cited by examiner

AUTOMATIC SLICE SELECTION IN MEDICAL IMAGING

RELATED APPLICATIONS

This application is the U.S. National Phase application under 35 U.S.C. § 371 of International Application No. PCT/EP2019/059491, filed on Apr. 12, 2019, which claims the benefit of European Application No. 18167156.1, filed Apr. 13, 2018. These applications are hereby incorporated by reference herein, for all purposes.

FIELD OF THE INVENTION

The invention relates to medical imaging, in particular to the identification of abnormal slices.

BACKGROUND OF THE INVENTION

In modern medical care, medical imaging techniques such as magnetic resonance imaging (MRI), computed tomography (CT), positron emission tomography (PET), and other techniques are becoming increasingly important. As time has progressed various imaging modalities are being used more and more. Also, the amount of data acquired by medical imaging scanners has also increased. In some hospitals radiologists will spend a large portion of their time visually scanning through large numbers of images after an imaging protocol has been completed.

SUMMARY OF THE INVENTION

The invention provides for a medical imaging system, a computer program product and a method in the independent claims. Embodiments are given in the dependent claims.

Embodiments of the invention may provide a means of reducing the workload when examining a three-dimensional medical image data. Embodiments may do this by first receiving an imaging modality of the image which identifies the type of image. For example, the imaging modality may identify the three-dimensional medical image data as a MRI image, a CT image, or other medical imaging modality. An anatomical view classification is then received. The anatomical view classification may for example identify the anatomy present in the three-dimensional medical image data. In another example, the anatomical view classification may identify the imaging protocol used. For example, the anatomical view classification may identify a particular type of MRI scan of the brain, a shoulder, or other anatomical structure.

The imaging modality and the anatomical view classification are then used to select a chosen abnormality detection module from a set of abnormality detection modules. The set of abnormality detection modules are each convolution neural networks that are trained for a particular imaging modality and a particular anatomical view classification. The chosen abnormality detection module is then used to check at least a portion of the slices of the three-dimensional medical image data to see if any are classified as abnormal. If any of the slices are abnormal then a predetermined selection criteria is used to choose a set of selected slices from the three-dimensional image data. The set of selected slices can for example be displayed on a user interface or identified for later inspection by the radiologist.

In one aspect the invention provides for a medical imaging system that comprises a memory for storing machine-executable instructions. The medical imaging system further comprises a processor for controlling the medical imaging system. The execution of the machine-executable instructions causes the processor to receive three-dimensional medical image data comprising multiple slices. Three-dimensional medical image data is data which can be used to either render a 3D volume or can be displayed as a number of two-dimensional slices of a three-dimensional volume. Execution of the machine-executable instructions further causes the processor to receive an imaging modality of the three-dimensional medical image data. The imaging modality may for example be the type of imaging scanner or apparatus that was used to acquire the three-dimensional medical image data.

Execution of the machine-executable instructions further causes the processor to receive an anatomical view classification of the three-dimensional medical image data. The anatomical view classification may for example indicate the type of imaging procedure that was used to acquire the three-dimensional medical image data or it may include a listing or list of anatomical regions which are within the three-dimensional medical image data. Execution of the machine-executable instructions further causes the processor to select a chosen abnormality detection module from a set of abnormality detection modules using the imaging modality and the anatomical view classification. Each of the abnormality detection modules is a convolution neural network trained for identifying if at least a portion of the multiple slices is either normal or abnormal. In some specific examples the at least a portion of the multiple slices is each of the multiple slices. References to "each of the multiple slices" may also be interpreted as at least a portion of the multiple slices.

By having a set of abnormality detection modules the chosen abnormality detection module can be trained for the particular imaging modality and also the particular anatomical view represented in the three-dimensional medical image data. Execution of the machine-executable instructions further causes the processor to classify the at least a portion of the multiple slices as normal or abnormal using the abnormality detection module.

For example, each of the slices may be input into the convolution neural network and the output is that the slices are classified as either normal or abnormal. Execution of the machine-executable instructions further causes the processor to choose a set of selected slices from multiple slices if a predetermined number of the multiple slices are classified as abnormal according to a predetermined selection criteria. In some examples the predetermined number of the multiple slices is one. It is understood herein that "a predetermined number of the multiple slices" can be replaced with "any of the multiple slices."

If the three-dimensional medical imaging data comprises any slices which are identified as abnormal by the convolution neural network then a group of the three-dimensional medical image data is chosen as the set of selected slices.

This embodiment may be beneficial because the set of selected slices may be chosen such that a physician is able to identify one or more of the multiple slices that were identified as abnormal. This may assist the radiologist or other technical individual looking through the three-dimensional medical image data to find abnormalities.

In another embodiment execution of the machine-executable instructions further cause the processor to calculate an entropy of each of the multiple slices. Execution of the machine-executable instructions further cause the processor to calculate a mean squared error intensity variation between adjacent slices for each of the multiple slices. Execution of the machine-executable instructions further cause the processor to add a chosen slice of the multiple slices to the set of selected slices if the ratio of the entropy for the slice to mean squared error intensity variation between the adjacent slices is above a predetermined information content threshold. In this embodiment slices which have a high entropy relative to the mean squared error intensity variation are chosen. This may be beneficial because the image may contain a larger than usual amount of information depending upon how the predetermined information content threshold is chosen. This may select slices which have more details or information that may be beneficial for an operator to examine.

In another embodiment the abnormality detection module is configured for generating a feature vector for each of the multiple slices. The calculation of a feature vector is any normal feature of a convolution neural network. Execution of the machine-executable instructions causes the processor to calculate an Euclidean distance between the feature vector of adjacent slices for each of the multiple slices. Execution of the machine-executable instructions further cause the processor to calculate a likelihood measure for each of the multiple slices by inputting the feature vector of each of the multiple slices into a Gaussian mixture model. The Gaussian mixture model is trained to determine the probability if the feature vector is normal and abnormal. Execution of the machine-executable instructions further causes the processor to add a selected slice from the multiple slices to the set of selected slices if the ratio of the likelihood measure to the Euclidean distance is greater than a predetermined abnormality measure threshold. This embodiment may be beneficial because slices which have a high probability of containing abnormalities as identified by the Gaussian mixture model may be selected.

In another embodiment execution of the machine-executable instructions further causes the processor to train the Gaussian mixture model using feature vectors derived from the abnormality detection module. This embodiment may be beneficial because it may provide for an efficient and effective way of training the Gaussian mixture model.

In another embodiment execution of the machine-executable instructions further causes the processor to determine an imaging modality of the three-dimensional medical image with an imaging modality classifier. For example, a neural network could be trained to receive medical images as input and then output the type of imaging modality. In other examples the imaging modality classifier could be code which looks at headers or meta data or log files and uses this information to determine the imaging modality.

In another embodiment the imaging modality classifier is configured for determining the imaging modality using any one of the following: processing a report or log file using natural language processing, extracting the imaging modality from a DICOM header, and receiving the imaging modality from a health information system.

In another embodiment execution of the machine-executable instructions further causes the processor to determine an anatomical view classification using an anatomical classification module. The anatomy classification module is a trained convolution neural network. In this embodiment a trained convolution neural network may be used to identify the particular anatomical view of the three-dimensional medical image data. This may be useful because it may be used for then pre-selecting the chosen abnormality detection module.

In another embodiment the imaging modality is any one of the following: a magnetic resonance imaging, a positron emission tomography, single photon emission tomography, ultrasound, X-ray, computer tomography, and endoscopy.

In another embodiment execution of the machine-executable instructions further cause the processor to receive multiple sets of three-dimensional medical image data.

In another embodiment the medical imaging data comprises a display. Execution of the machine-executable instructions further cause the processor to display the set of selected files on the display. This may be beneficial because it may save the medical professional or operator from having to go through a large number of slices before finding an anomaly.

In another embodiment the medical imaging system comprises a display. Execution of the machine-executable instructions further cause the processor to display a selected portion of the three-dimensional medical image data on the display. The selected portion consists of the set of selected slices and of slices of the three-dimensional medical image data that are between the set of selected slices. In this embodiment the set of selected slices are displayed as well as the slices of medical image data that are between them. This may be beneficial because it may provide more information for the medical professional or operator to find abnormalities.

In another embodiment the medical imaging system comprises a medical imaging scanner configured for acquiring the three-dimensional medical image data. Execution of the machine-executable instructions further cause the processor to control the medical imaging scanner to acquire the three-dimensional medical image data.

In another embodiment the medical imaging scanner is any one of the following: a magnetic resonance imaging system, a positron emission tomography system, a single photon emission tomography system, an ultrasound imaging system, an X-ray system, a computer tomography system, and an endoscopy system.

In another aspect the invention provides for a method of operating a medical imaging system. The method comprises receiving three-dimensional medical image data comprising multiple slices. The method further comprises receiving an imaging modality of the three-dimensional medical image data. The method further comprises receiving an anatomical view classification of the three-dimensional medical image data. The method further comprises selecting a chosen abnormality detection module from a set of abnormality detection modules using the imaging modality and the anatomical view classification. Each of the abnormality detection modules is a convolution neural network trained for identifying if each of the multiple slices is either normal or abnormal. The method further comprises classifying each of the multiple slices as normal or abnormal using the abnormality detection module. The method further comprises choosing the set of selected slices from the multiple slices if any of the multiple slices are classified as abnormal according to a predetermined selection criteria.

In another aspect the invention provides for a computer program product comprising machine-executable instructions for execution by a processor controlling the medical imaging system. Execution of the machine-executable instructions further causes the processor to receive three-dimensional medical image data comprising multiple slices. Execution of the machine-executable instructions further causes the processor to receive an imaging modality of the three-dimensional medical image data. Execution of the machine-executable instructions further causes the processor to receive an anatomical view classification of the three-dimensional medical image data. Execution of the machine-executable instructions further cause the processor to select a chosen abnormality detection module from a set of abnormality detection modules using the imaging modality and the anatomical view classification. Each of the abnormality detection modules is a convolution neural network trained for identifying if each of the multiple slices is either normal or abnormal.

Execution of the machine-executable instructions further cause the processor to classify each of the multiple slices as normal or abnormal using the abnormality detection module. Execution of the machine-executable instructions further causes the processor to choose a set of selected slices from the multiple slices if any of the multiple slices are classified as abnormal according to a predetermined selection criteria.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data or magnetic resonance imaging data is defined herein as being the recorded measurements of radio frequency signals emitted by atomic spins using the antenna of a Magnetic resonance apparatus during a magnetic resonance imaging scan. A Magnetic Resonance Imaging (MRI) image or MR image is defined herein as being the reconstructed two or three-dimensional visualization of anatomic data contained within the magnetic resonance imaging data. This visualization can be performed using a computer. A magnetic resonance image is an example of medical image data or three-dimensional medical image data.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
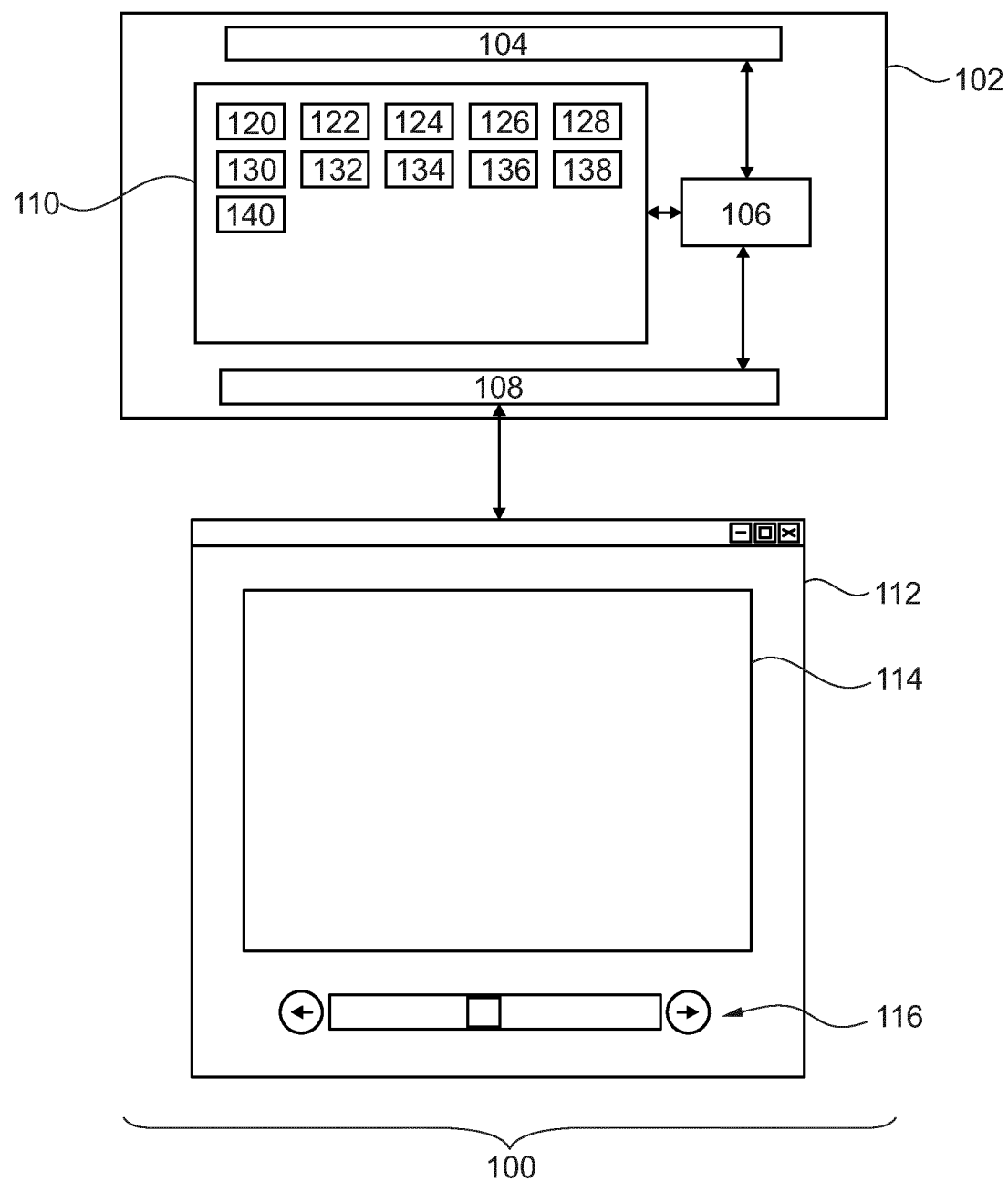
FIG. 1 illustrates an example of a medical imaging system.

FIG. 1 illustrates an example of a medical imaging system 100. The medical imaging system is shown as comprising a computer system 102. The computer system 102 has a hardware and/or network interface 104 that can be used for controlling other components and/or communicating with other computer systems via a network. The computer system 102 is also shown as comprising a processor 106 that is connected to the hardware or network interface 104 and also to the user interface 108 and a computer memory 110. The memory 110 may be any combination of memory which is accessible to the processor 106. This may include such things as main memory, cached memory, and also non-volatile memory such as flash RAM, hard drives, or other storage devices. In some examples the memory 110 may be considered to be a non-transitory computer-readable medium.

The user interface 108 may comprise a display that renders a graphical user interface 112. The graphical user interface 112 may have a region for rendering slices or two-dimensional images. There may also be a control 116 that allows an operator to flip through and view the renderings 114.

The computer memory 110 is shown as containing machine-executable instructions. The machine-executable instructions 120 enable the processor 106 to possibly control other components of the medical imaging system 100 and/or also to perform various computational and data processing tasks. The memory 110 is further shown as containing a three-dimensional medical image data 122. The three-dimensional medical image data may either have been acquired by an additional medical scanner or it may have been received via for example the network interface 104. The memory 110 is further shown as containing an imaging modality 124 that identifies the imaging modality of the three-dimensional medical image data 122. The memory 110 is further shown as containing an anatomical view classification 126 that classifies the anatomy viewed or imaged in the three-dimensional medical image data 122.

The memory 110 is further shown as containing a set of abnormality detection modules 128. The set of abnormality detection modules 128 is a set of convolution neural networks that have been trained to recognize abnormalities for different imaging modalities and different anatomical views. The memory 110 is further shown as containing a chosen abnormality detection module 130 that was chosen from the set of abnormality detection modules using the imaging modality 124 and the anatomical view classification 126.

The memory 110 is further shown as containing a classification of each of the multiple slices 132 of the three-dimensional medical image data 122 that was performed using the chosen abnormality detection module 130. The classification for each of the slices 132 classifies each of the slices as either being normal or abnormal. If any of the slices are identified as being abnormal then a set of predetermined selection criteria 134 is used to select a set of selected slices 136. The predetermined selection criteria 134 and the set of selected slices 136 are shown as being stored in the memory 110. The slices selected by the predetermined selection criteria 134 may then be used to select slices of the three-dimensional medical image data to display on the graphical user interface 112 the rendering of the slice 114.

The memory 110 is also shown as containing an optional imaging modality classifier 138 that may be used to provide the imaging modality 124. The memory 110 is also shown as containing an optional anatomy classification module 140 that may be used for providing the anatomical view classification 126.

Figure 2:
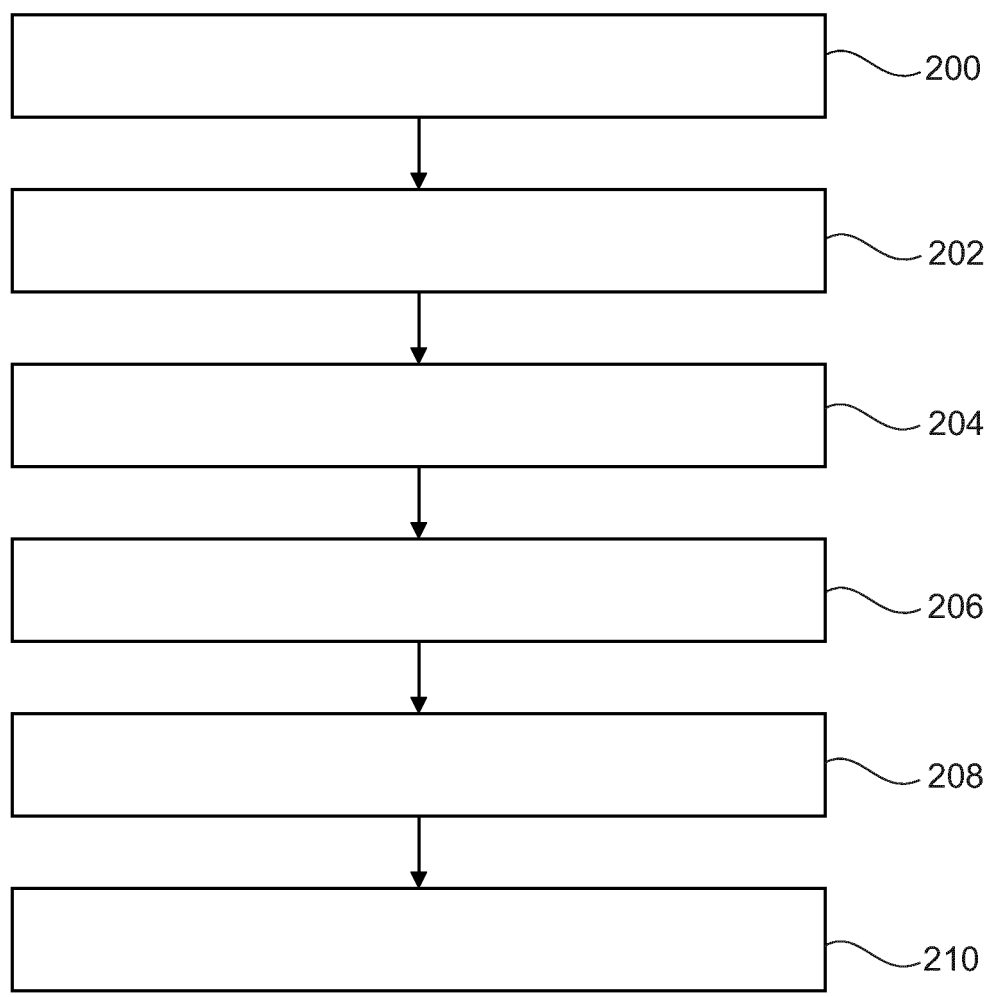
FIG. 2 shows a flow chart which illustrates an example of a method of operating the medical imaging system of FIG. 1.

FIG. 2 shows a flow chart which illustrates a method of operating the medical instrument of FIG. 1. First is step 200, three-dimensional medical imaging data comprising multiple slices is received. Next in step 202 an imaging modality of the three-dimensional medical imaged data is received. The imaging modality may be an identification of the type of medical imaging scanner used to acquire the three-dimensional medical image data. Then in step 204 an anatomical view classification of the three-dimensional medical image data is received. The anatomical view classification may be an identification of anatomical structures imaged in the three-dimensional medical image data or it could be an identification of a type of imaging protocol used during acquisition of the three-dimensional medical image data. Next in step 206 a chosen abnormality detection module is selected from a set of abnormality detection modules using the imaging modality and the anatomical view classification. Each of the abnormality detection modules is a convolution neural network trained for identifying if each of the multiple slices as either normal or abnormal. Then in step 208 each of the multiple slices is classified as being as normal or abnormal using the abnormality detection module. Finally, in step 201 a set of selected slices is chosen from the multiple slices if any of the multiple slices are classified as abnormal according to a predetermined selection criteria.

Figure 3:
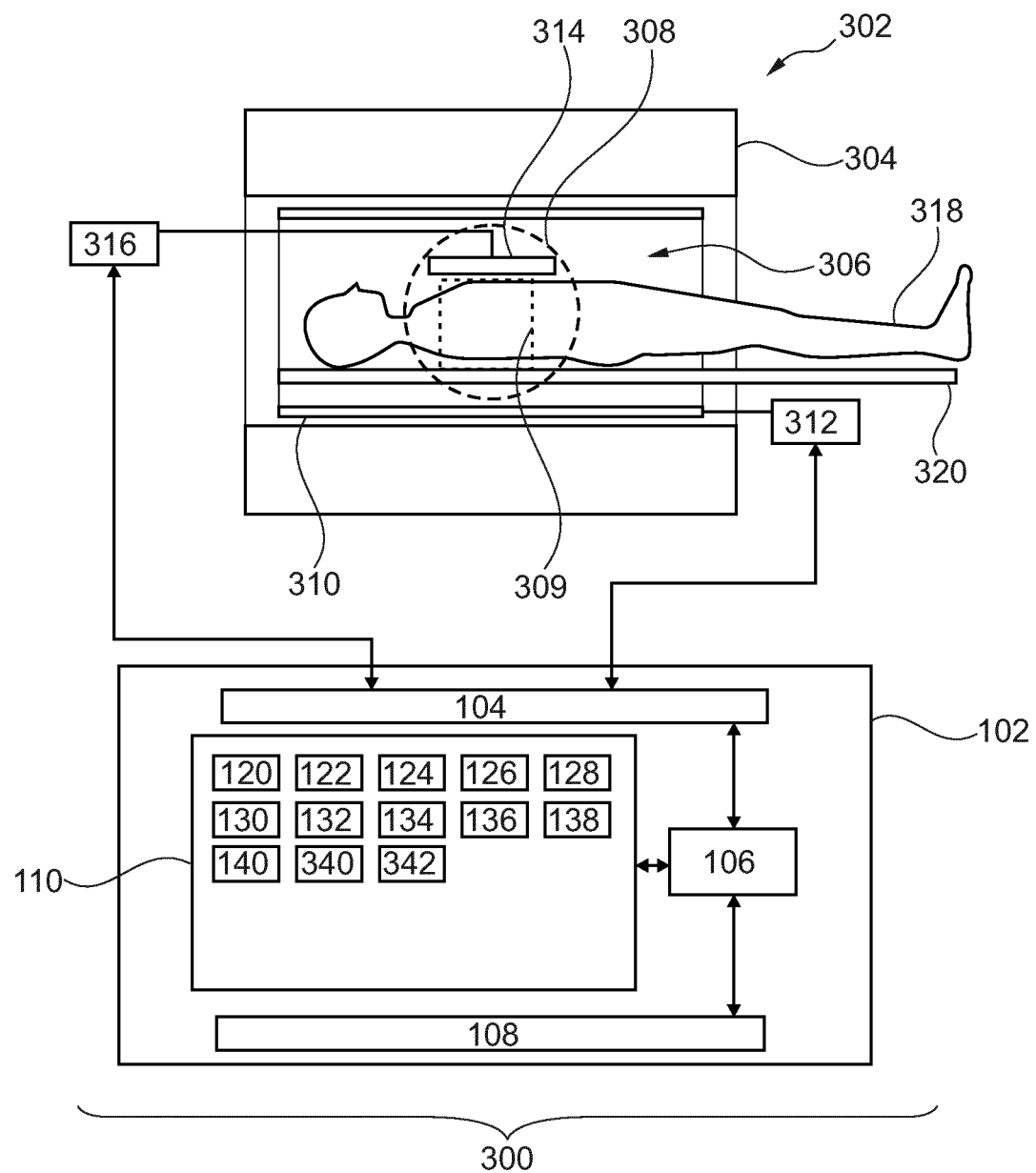
FIG. 3 illustrates a further example of a medical imaging system.

FIG. 3 shows a further example of a medical imaging system 300. The medical imaging system 300 is similar to the medical imaging system 100 except that the medical imaging system 300 additionally comprises a magnetic resonance imaging system 302. The magnetic resonance imaging system 302 is intended to be a generic example of a medical imaging scanner. The medical imaging system 300 can additionally comprise more than one additional medical imaging scanner and could for example be one or more of a magnetic resonance imaging system, a positron emission tomography system, a single photon emission tomography system, an ultrasound imaging system, an X-ray system, a computer tomography system and an endoscopy system.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet 304 there is an imaging zone 308 where the magnetic field is strong and uniform enough to perform magnetic resonance imaging. A region of interest 309 is shown within the imaging zone 308. The magnetic resonance data that is acquired typically acquired for the region of interest. A subject 318 is shown as being supported by a subject support 320 such that at least a portion of the subject 318 is within the imaging zone 308 and the region of interest 309.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically, magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise, the transceiver 316 may also represent a separate transmitter and receivers. The radio-frequency coil 314 may also have multiple receive/transmit elements and the radio frequency transceiver 316 may have multiple receive/transmit channels. For example, if a parallel imaging technique such as SENSE is performed, the radio-frequency could 314 will have multiple coil elements.

The memory 110 is shown as additionally comprising pulse sequence commands 340. The pulse sequence commands 340 are instructions or data which can be converted into such instructions that may be used for controlling the magnetic resonance imaging system 302 to acquire magnetic resonance imaging data. The memory 110 is further shown as containing magnetic resonance imaging data 342 that was acquired by controlling the magnetic resonance imaging system 302 with the pulse sequence commands 340. The execution of the machine-executable instructions 120 may be used to reconstruct the three-dimensional medical image data 122 from the magnetic resonance imaging data 342.

With the increasing demand on the radiologist to handle multiple reports and provide their diagnosis with in a limited time span is leading to over burdening of the health care system. In this invention, we provide a solution to auto identify the clinically significant slices and anatomical regions from the scan and there by identify the clinical changes in those scans, which have information to make diagnosis. Further, the slices containing only the clinically significant information are identified and registered with region of interest marking for further diagnostic decision with reduced time spent on visualization, hence improving the throughput.

Both CT and MRI utilization and the number of images being collected for those exams have increased significantly in recent years, according to a recent study published in Academic Radiology. The authors believe this could potentially lead to an increase in errors made by overworked radiologists. Robert J. McDonald, MD, from the department of radiology at the Mayo Clinic in Rochester, Minn., and colleagues performed the study, examining the total number of images for every CT and MRI exam performed at their institution between 1999 and 2010. In that timespan, over 1.5 million CT and MRI exams were performed by a radiologist. From 1999 to 2010, CT utilization increased 68%, MRI utilization increased 85%, and overall utilization increased 75%.

The authors determined that over 539 million images were collected from exams during the study period. CT exams increased from 82 images per exam in 1999 to 679 images per exam in 2010. MRI exams increased from 164 images per exam in 1999 to 570 images per exam in 2010.

However, hiring additional radiologists to assist with this increase in utilization and images is not enough. In 1999, a radiologist interpreting CT scans was required to interpret 2.8 images per minute. In 2010, that same number was over 19 images per minute. Likewise, a radiologist interpreting MRI scans was required to interpret 3 images per minute in 1999, but that number jumped to almost 12 per minute in 2010. The modern radiologist must now interpret many times more examination images when compared to similar examinations performed 10-20 years ago. Although these advances in sensitivity and specificity are thought to translate to improved patient care, these increasing imaging volumes are placing an ever-increasing burden on the practicing radiologist. As the workload continues to increase, there is concern that the quality of the health care delivered by the radiologist will decline in the form of increased detection errors because of increased fatigue and stress. Hence, we provide a technical solution where in it's possible to see only the clinically relevant scans to the out of all the scans obtained so that radiologist is not overburdened as well as he can spend lesser time to make diagnostics decision and also more accurate Examples may have one or more of the following advantages:
1. Rather than radiologist having to go through all the scan slices of the subject, our solution helps to identify only the specific slices that are clinically significant that's needs to be displayed first to the radiologist rather than the entire scan volume
2. Helps in reducing the time spent by radiologist in analyzing all the slices of the scan
3. The system also provides the suggestions for the other clinical findings (if any) based on the prior history and the current examination in additions to the requested examinations, thereby reducing the scan repeats and improving the diagnostic quality
4. The system also stitches only the slices which has clinically significant information into a visualization volume.

Examples may have one or more of the following features:
1. Imaging Modality type classification module (imaging modality classifier) that determines the imaging modality
2. Anatomy classification module that determines the anatomical view classification
3. Abnormality detection module that classifies a slice as being either normal or abnormal
4. Abnormal slice selection module (predetermined selection criteria)
5. Orchestrator module (machine executable instructions)

Figure 4:
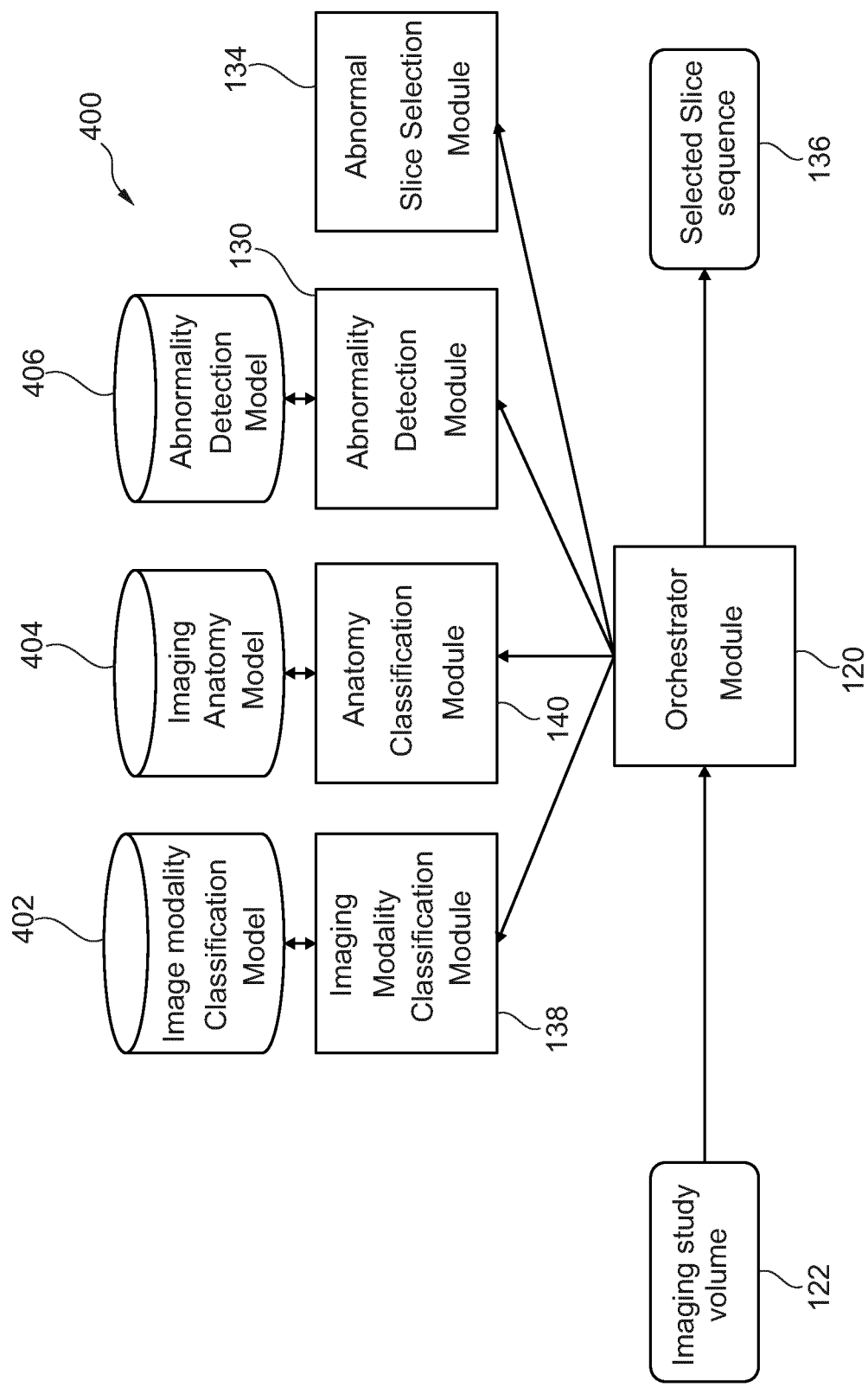
FIG. 4 illustrates a further example of a medical imaging system.

FIG. 4 illustrates a high level and functional diagram of a further example of a medical imaging system 400. In FIG. 4 there is an orchestrator module 120 that controls the process and operations of the medical imaging system 400. The orchestrator module 120 may be equivalent to the machine-executable instructions 120. The orchestrator module 120 receives an image study volume 122. The image study volume 122 may be processed by an imaging modality classification module 138, an anatomy classification module 140, and an abnormality detection module 130. The imaging modality classification module 138 may use an imaging modality classification model 402. The anatomy classification module 140 may use an imaging anatomy model 404. The abnormality detection module 130 may use an abnormality detection model 406. If there are any abnormalities in the slice the orchestrator module may use an abnormal slice selection module 134. The abnormal slice selection module 134 may be equivalent to the predetermined selection criteria 134 that is used by the examples in FIGS. 1 and 3. The output of the abnormal slice selection module 134 is a selected slice sequence 136 which is equivalent to the set of selected slices.

Imaging modality classification module may for example be implemented by detecting the DICOM headers or by processing the reports using NLP. Also we do consider the information from the RIS and HIS to arrive at the modality type as well as associated investigations.

Figure 5:
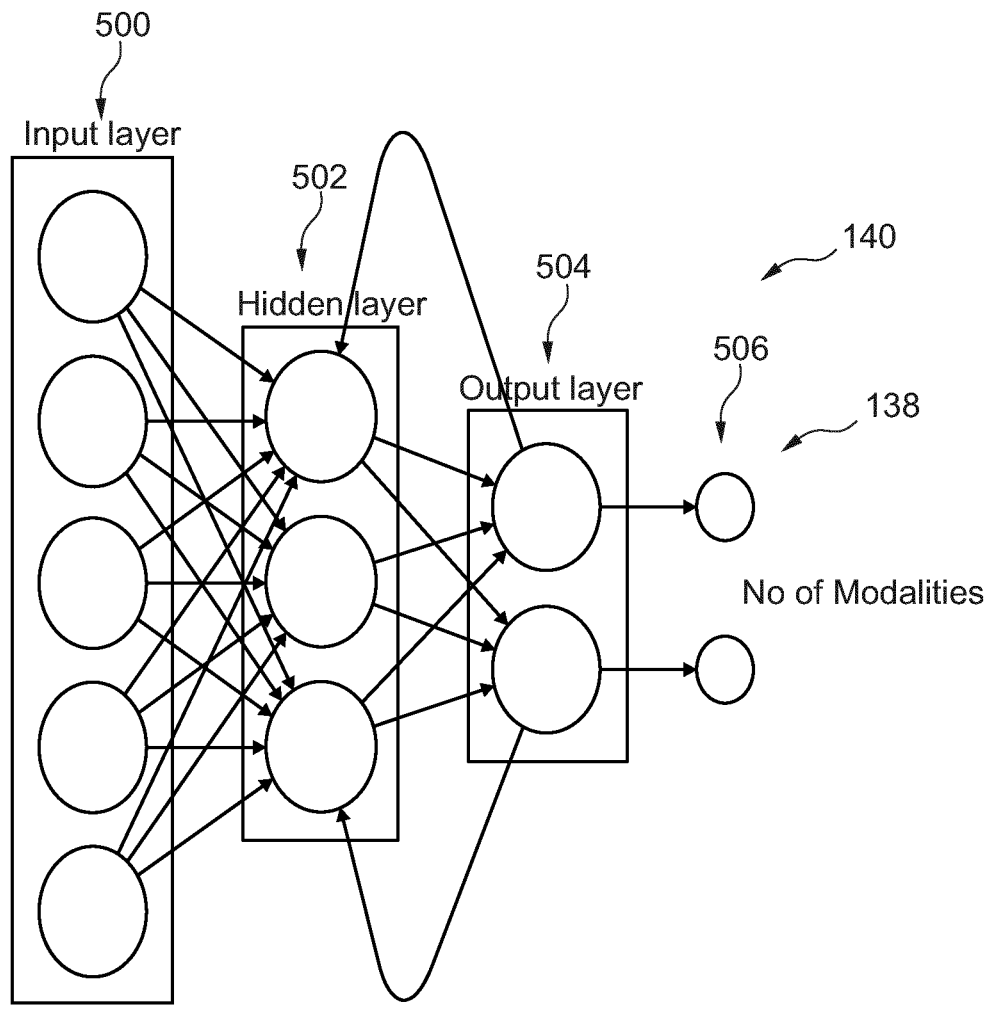
FIG. 5 illustrates an example of a neural network.

The anatomy classification module may be used to identify the slices of the relevant anatomy present in the scan. For instance, in a MRI Brain image the module would identify the anatomy as Brain. We use convolution neural network as in the previous module with only difference being the last softmax layer has the dimensionality as the number of anatomy regions per imaging modality. FIG. 5 below depicts the CNN architecture FIG. 5 illustrates an idealized convolution neural network that may be used for implementing either the anatomy classification module and/or in some cases the imaging modality classifier 138. There is an input layer 500 for inputting the image and then a number of hidden layers 502. There is then an output layer 504 which provides an output 506. In the case of the anatomy classification module 140 there is one output 506 for each of the possible image modes. For example, one may indicate a particular image of a knee, brain or other anatomy. In the case of the imaging modality classifier 138 the imaging modality may be indicated by multiple outputs 506. For example, there may be one output that indicates a magnetic resonance image and another output indicates another type of image such as a CT image.

Figure 6:
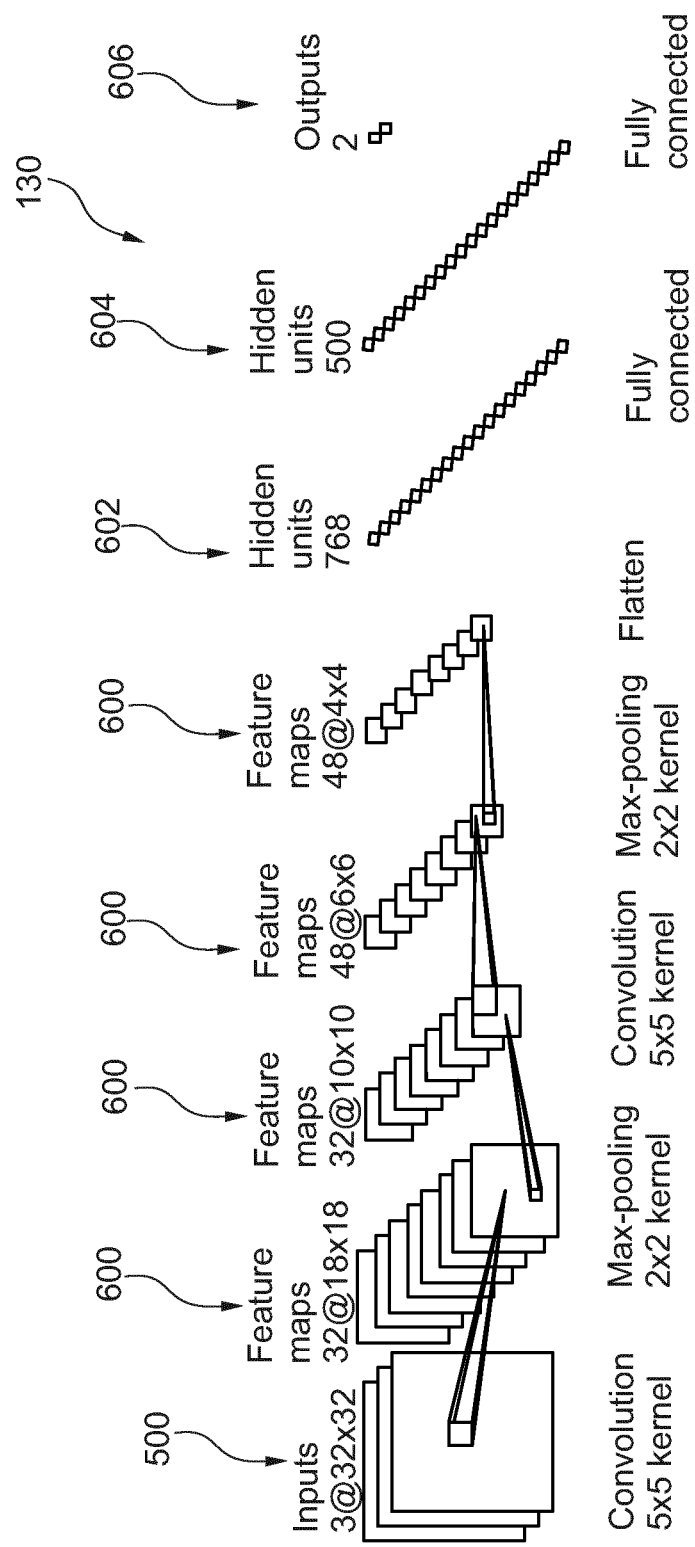
FIG. 6 illustrates a further example of a neural network.

The abnormality detection module may be used to identify if there is any abnormality present in the medical image of the anatomy of interest, which is identified by using step 2. For instance, in a MRI brain study there might be normal studies as well as abnormal studies like tumors, hemorrhage etc. We use the convolution neural network as in the previous module with only difference being the last softmax layer has two nodes as it is two class problem (normal vs abnormal image). FIG. 6 below depicts the architecture FIG. 6 illustrates a general implementation of a convolution neural network that may be used to implement the chosen abnormality detection module 130. The neural network 130 again has an input and then there are a number of future maps 600. This then feeds to hidden units 602 and hidden units 604. The hidden units 604 may be considered to be a feature vector. The feature vector 604 is then used to provide the outputs 606. In this example one output would indicate that the image is normal and the other output would be used to indicate if the image is abnormal.

The slice selection module may be used to identify the clinically significant slices from the whole volume of images, using one or more of the flowing method steps:
1. A two class GMM mixture model is trained on the featured derived from the abnormality detection CNN.
2. Euclidean distance between the feature vectors of successive slices (ED), the intensity variations between the slices through mean squared error (MSE), entropy of a slice (ENT) and the likelihood measure (LLM) of an individual slice with respect to the normal/abnormal anatomy are computed. All the measure are computed as follow:

$$ED = \frac{1}{D}\sqrt{\sum_{i=2}^{D}(FV_{i-1} - FV_i)^2}$$

Where, $FV_{i-1}$ & $FV_i$ are the features vectors of 'i−1' and '$i^{th}$' slices and 'D' is the dimension of feature vectors.

$$MSE = \frac{1}{MN}\sum_{j=1}^{M}\sum_{k=1}^{N}[I_{i-1}(j,k) - I_i(j,k)]^2$$

Where, $I_{i-1}$ & $I_i$ are the intensity values of two successive frames.

$$ENT = -\sum_{O \subset \Omega} p_o(I)\ln(p_o(I))$$

Where, $p_o(.)$ is the probability density function for intensity value 'O' and 'Ω' is the set of all possible grey values in 'I'.

$$LLR = \log[p(FV|S_A)] - \log[p(FV|S_N)]$$

Where, the '$S_N$', '$S_A$' are the Gaussian mixture models of normal and abnormal cases derived from Step.1 and '$F_V$' is the feature vector.

A first possible set of slices are selected based on the ratio of the entropy to MSE. Since the MSE is inversely related to the similarity of images and entropy, information is directly related to the content of the image. That is, $$SL_1 = \frac{ENT}{\log(MSE)}$$

The set of slices are selected based on the predefined threshold i.e., $SL_1 > Th_1$. (b) A second set of slices are selected based on the ratio of the LLR to ED. Since the ED is inversely related to the similarity of images and LLR, information is directly related to the content (normal/abnormal) of the image. That is, $$SL_2 = \frac{LLR}{\log(ED)}$$

The set of slices are selected based on the predefined threshold i.e., $ST_2 > 0$ & $ST_2 > Th_2$.

The above shown normalizations are advantageous, because they may prevent ill conditioning and increase stability. The normalization is carried out to capture the inherent relation between ENT and MSE; LLR and ED. The resulting feature vector provides a better discrimination between significant and non-significant slices.

Finally, one or both of the sets of slices are provided to the user for visualization. Since first set of slices are selected based only on the information content, whereas second set of slices selected are more related to abnormal content.

The orchestrator module may be used for training the modules and dynamic deployment of models. The orchestrator module could automate the process of selecting volume from medical studies. The orchestrator part in the training phase takes an input a set of volumes of various modalities along with associated labels regarding Modality, Anatomy and abnormality. The orchestrator component then sets up the initial configuration for the various modules during the training process. In the testing phase the orchestrator component would take as input either a medical study volume or set of medical study volumes and then apply the appropriate model at each of the modules to generate clinically significant volumes.

In some examples, implementation may take place in two phases: A) Training Phase and B) Deployment Phase
A) Training Phase:
In the training phase the input to the system is a set of medical study volumes along with associate labels like modality, anatomy, abnormality. These medical study volumes are acquired from various imaging modalities like CT, MR etc.

The orchestrator component takes as input this of medical study volumes along with associate labels like modality, anatomy, abnormality. The imaging volumes are classified into various imaging modality class using the modality information present as ground truth labels. Similar for each of the modality class the imaging volumes are further classified into respective anatomies. The slices of the volumes are further classified into normal vs abnormal classes On the completion of all of the training phase, a hierarchy of classification models are generated and the orchestrator component stores these models in appropriate model databases.

B) Deployment Phase:

In the deployment phase, the goal is to generate clinically relevant slices for imaging volume. The orchestrator component takes an imaging study volume as an input and then sends the slices to the imaging modality classification module. It then classifies the imaging volume to a modality. The orchestrator component then selects the appropriate anatomy classification model based on the predicted modality from the modality classification module an instantiates the anatomy classification module.

The anatomy classification module predicts the anatomy. The orchestrator then instantiates the abnormality module with the appropriate abnormality detection model based on predicted anatomy and modality from the previous stages for generating the abnormal slices. The slice selection module then selects appropriate slices for the study. Please find below diagram depicting this process for CT modality and Brain Anatomy.

Figure 7:
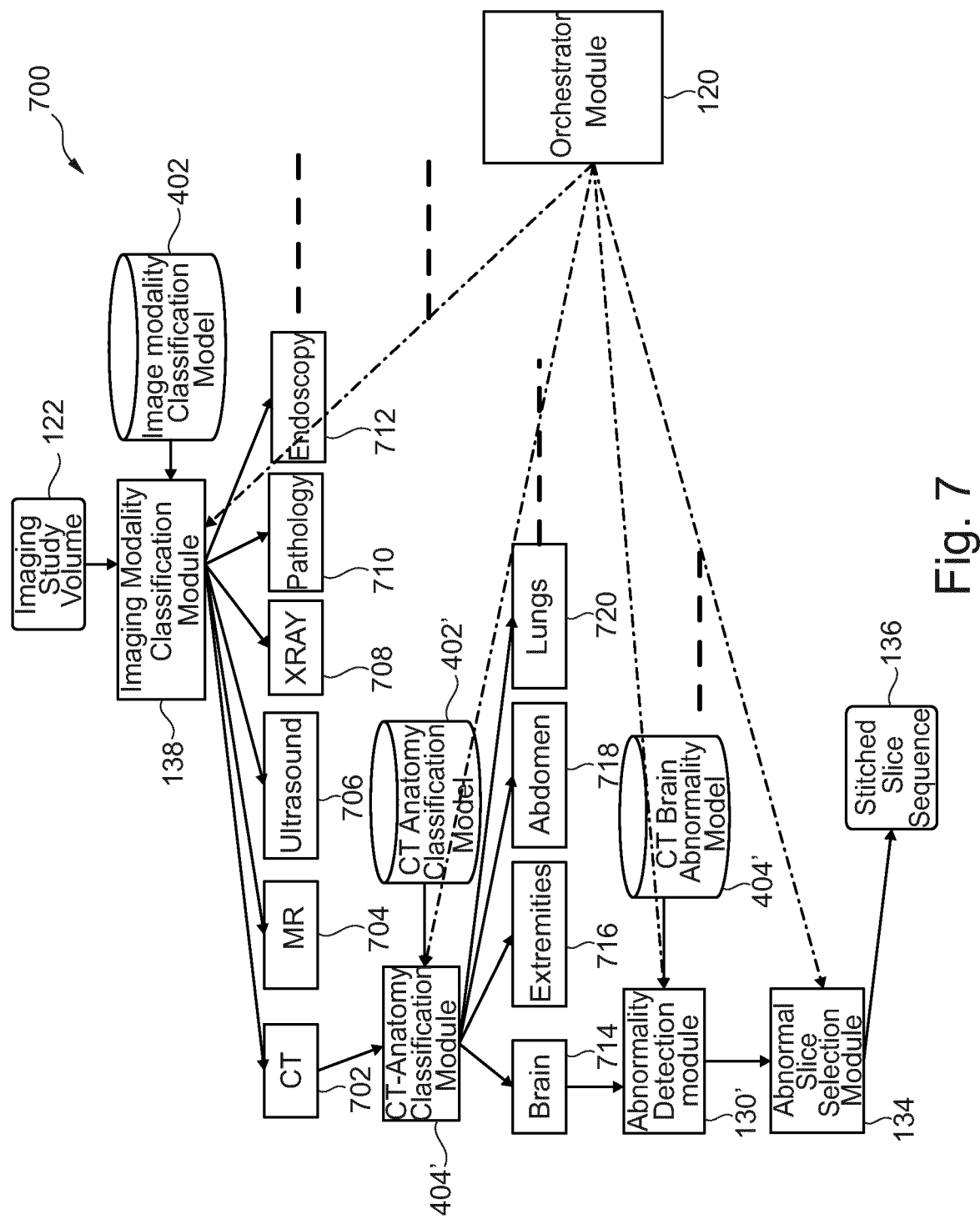
FIG. 7 illustrates a further example of a medical imaging system.

FIG. 7 illustrates a further example of a medical imaging system 700. The depiction in FIG. 7 is functional and is similar to the medical imaging system 400 in FIG. 4. In this example again the medical imaging system receives the imaging study volume 122. This is then first passed to an imaging modality classification module 138 that uses an imaging modality classification model 402. The imaging modality classification module is able to identify in this example a number of different imaging modalities such as CT, MR, ultrasound 706, X-ray 708, pathology 710 and endoscopy 712. In this particular example the imaging study volume is a CT image so the imaging study volume is then passed to the CT-anatomy classification module 404'. The CT-anatomy classification module 404' uses a CT-anatomy classification model 402'. In this example the CT-anatomy classification module 404' identifies the imaging study volume 122 as that of a brain 714. There are also a number of other possible examples in this case, it could be a brain 714, the extremities 716, the abdomen 718 or the lung 720. As it is the brain 714 it is then passed to a specific abnormality detection module 130' that is used for the brain.

The abnormality detection module 130' uses a CT brain abnormality model 404'. The abnormality detection module 130' identified one or more slices as being abnormal so it is then passed to the abnormal slice selection module 134 to provide the set of selected slices 136. In this example they are a stitched slice sequence. In the stitched slice sequence there are abnormal slices which are selected to be displayed to the operator or physician and then also the intermediate slices between those slices so that the physician or operator has complete volumes to examine.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical imaging system
102 computer system
104 hardware/network interface
106 processor
108 user interface
110 computer memory
112 graphical user interface
114 rendering of slice
116 control to flip through slices
120 machine executable instructions
122 three dimensional-medical image data
124 imaging modality
126 anatomical view classification
128 set of abnormality detection modules
130 chosen abnormality detection module
132 classification each of the multiple slices
134 predetermined selection criteria
136 set of selected slices
138 imaging modality classifier
140 anatomy classification module
200 receive three-dimensional medical image data comprising multiple slices
202 receive an imaging modality of the three-dimensional medical image data
204 receive an anatomical view classification of the three-dimensional medical image data
206 select a chosen abnormality detection module from a set of abnormality detection modules using the imaging modality and the anatomical view classification
208 classify each of the multiple slices as normal or abnormal using the abnormality detection module
210 choose a set of selected slices from the multiple slices if any of the multiple slices are classified as abnormal according to a predetermined selection criteria
300 medical imaging system
302 magnetic resonance imaging system
304 magnet
306 bore of magnet
308 imaging zone
309 region of interest
310 magnetic field gradient coils
312 magnetic field gradient coil power supply
314 radio-frequency coil
316 transceiver
318 subject
320 subject support 340 pulse sequence commands
342 magnetic resonance imaging data
400 medical imaging system
402 image modality classification model
402 imaging anatomy model
402' CT anatomy classification module
404 abnormality detection model
404' CT brain abnormality model
500 input layer
502 hidden layer
504 output layer
506 output
600 feature map
602 hidden units
604 feature vector
606 outputs
700 medical imaging system
702 CT
704 MR (MRI)
706 ultrasound
708 x-ray
710 pathology
712 endoscopy
714 brain
716 extermities
718 abdomen
720 lungs

The invention claimed is:

1. A medical imaging system comprising:
a memory for storing machine executable instructions;
a processor for controlling the medical imaging system, wherein execution of the machine executable instructions causes the processor to:
receive three-dimensional medical image data comprising multiple slices;
receive an imaging modality of the three-dimensional medical image data;
receive an anatomical view classification of anatomy in the three-dimensional medical image data;
select a chosen abnormality detection module from a set of abnormality detection modules using the imaging modality and the anatomical view classification, wherein each of the abnormality detection modules is a convolution neural network trained for generating a feature vector for at least a portion of the multiple slices and identifying the at least a portion of the multiple slices as either normal or abnormal using the feature vector;
classify the at least a portion of the multiple slices as normal or abnormal using the abnormality detection module; and
choose a set of selected slices from the multiple slices according to a predetermined selection criteria if a predetermined number of the multiple slices are classified as abnormal.

2. The medical imaging system of claim 1, wherein execution of the machine executable instructions further causes the processor to:
calculate an entropy of the at least a portion of the multiple slices;
calculate a mean squared error intensity variation between adjacent slices for the at least a portion of the multiple slices; and
add a chosen slice of the multiple slices to the set of selected slices if the ratio of the entropy for the slice to the mean squared error intensity variation between adjacent slices is above a predetermined information content threshold.

3. The medical imaging system of claim 1, wherein execution of the machine executable instructions further causes the processor to train a Gaussian mixture model using feature vectors derived from the chosen abnormality detection module.

4. The medical imaging system of claim 1, wherein execution of the machine executable instructions further causes the processor to determine the imaging modality of the three-dimensional medical image data with an imaging modality classifier.

5. The medical imaging system of claim 4, wherein the imaging modality classifier is configured for determining the imaging modality by processing a report or log file using natural language processing.

6. The medical imaging system of claim 4, wherein the imaging modality classifier is configured for determining the imaging modality by extracting the imaging modality from a DICOM header or receiving the imaging modality from a health information system.

7. The medical imaging system of claim 4, wherein the imaging modality classifier is a trained convolution neural network.

8. The medical imaging system of claim 1, wherein execution of the machine executable instructions further causes the processor to determine the anatomical view classification using an anatomy classification module, wherein the anatomy classification module is a trained convolution neural network.

9. The medical imaging system according to claim 8, wherein a model is used by the anatomy classification module and the chosen abnormality detection module.

10. The medical imaging system of claim 1, wherein the imaging modality is any one of the following: magnetic resonance imaging, computer tomography, positron emission tomography, ultrasound, x-ray, and endoscopy.

11. The medical imaging system of claim 1, wherein execution of the machine executable instructions further causes the processor to:
receive multiple sets of three-dimensional medical image data, and
choose the set of selected slices for the at least a portion of the multiple sets of three-dimensional medical image data.

12. The medical imaging system of claim 1, wherein the medical imaging system comprises a display, and wherein execution of the machine executable instructions further causes the processor to display the set of selected slices on the display.

13. The medical imaging system of claim 1, wherein the medical imaging system comprises a display, wherein execution of the machine executable instructions further causes the processor to display a selected portion of the three-dimensional medical image data on the display, wherein the selected portion consists of the set of selected slices and slices of the three-dimensional medial image data that are between the set of selected slices.

14. The medical imaging system of claim 1, wherein the medical imaging system comprises a medical imaging scanner configured for acquiring the three-dimensional medical image data, wherein execution of the machine executable instructions further causes the processor to control the medical imaging scanner to acquire the three-dimensional medical imaging data.

15. The medical imaging system of claim 14, wherein the medical imaging scanner is any one of the following: a magnetic resonance imaging system, positron emission tomography system, a single photon emission tomography system, an ultrasound imaging system, an x-ray system, a computed tomography system, and an endoscopy system.

16. The medical imaging system of claim 1, wherein the anatomical view classification identifies a body part present in the three-dimensional medical image data for use in selection of the chosen abnormality detection module.

17. The medical imaging system of claim 16, wherein the body part is an organ.

18. The medical imaging system of claim 16, wherein the anatomical view classification identifies an imaging protocol for use in selection of the chosen abnormality detection module.

19. The medical imaging system according to claim 1, wherein execution of the machine executable instructions causes the processor to: calculate a likelihood measure for the at least a portion of the multiple slices; add a selected slice of the multiple slices to the set of selected slices if the ratio of the likelihood measure to the Euclidean distance is greater than a predetermined abnormality measure threshold.

20. The medical imaging system according to claim 1, wherein the chosen abnormality detection module is instantiated with an abnormality detection model based on predicted modality and anatomy.

21. The medical imaging system according to claim 20, wherein an anatomy classification model is selected based on a predicted modality from a modality classification module and an anatomy is predicted by an anatomy classification module using the anatomy classification model.

22. The medical imaging system according to claim 1, wherein a plurality of abnormal slices are stitched together into a visualization volume.

23. The medical imaging system according to claim 1, wherein the instructions cause the processor to provide suggestions for other clinical findings based on the selected slices and prior history of a same patient.

24. A method for operating a medical imaging system, wherein the method comprises
receiving three-dimensional medical image data comprising multiple slices;
receiving an imaging modality of the three-dimensional medical image data;
receiving an anatomical view classification of the three-dimensional medical image data;
selecting a chosen abnormality detection module from a set of abnormality detection modules using the imaging modality and the anatomical view classification, wherein each of the abnormality detection modules is a convolution neural network trained for identifying at least a portion of the multiple slices as either normal or abnormal;
classifying the at least a portion of the multiple slices as normal or abnormal using the abnormality detection module; and
choosing a set of selected slices from the multiple slices according to a predetermined selection criteria if a predetermined number of the multiple slices are classified as abnormal.

25. A computer program product comprising machine executable instructions for execution by a processor controlling a medical imaging system, wherein execution of the machine executable instructions causes the processor to:
receive three-dimensional medical image data comprising multiple slices;
receive an imaging modality of the three-dimensional medical image data;
receive an anatomical view classification of the three-dimensional medical image data;
select a chosen abnormality detection module from a set of abnormality detection modules using the imaging modality and the anatomical view classification, wherein each of the abnormality detection modules is a convolution neural network trained for identifying at least a portion of the multiple slices as either normal or abnormal;
classify the at least a portion of the multiple slices as normal or abnormal using the abnormality detection module; and
choose a set of selected slices from the multiple slices according to a predetermined selection criteria if a predetermined number of the multiple slices are classified as abnormal.

26. The computer program product according to claim 25, wherein the processor controls a medical imaging scanner to acquire the three-dimensional medical image data or controls an external computing device.

* * * * *